US008845602B2

(12) United States Patent
Blomet et al.

(10) Patent No.: US 8,845,602 B2
(45) Date of Patent: Sep. 30, 2014

(54) INDIVIDUAL PORTABLE DEVICE FOR EYE BATH

(75) Inventors: Joël Blomet, Paris (FR); Patrick Cailly, Paris (FR); Michel Hanek, Paris (FR)

(73) Assignee: Prevor International, Paris (FR)

( * ) Notice: Subject to any disclaimer, the term of this patent is extended or adjusted under 35 U.S.C. 154(b) by 1624 days.

(21) Appl. No.: 11/934,929

(22) Filed: Nov. 5, 2007

(65) Prior Publication Data

US 2008/0141454 A1 Jun. 19, 2008

(30) Foreign Application Priority Data

Nov. 3, 2006 (FR) ..................................... 06 09629

(51) Int. Cl.
*A61H 35/02* (2006.01)
*A61M 35/00* (2006.01)
*B65D 41/00* (2006.01)
*B65D 41/04* (2006.01)

(52) U.S. Cl.
CPC ............ *A61H 35/02* (2013.01); *B65D 41/0428* (2013.01)
USPC ................................ 604/301; 215/343; 4/620

(58) Field of Classification Search
CPC ............................ B65D 41/0428; A61H 35/02
USPC ................. 601/13; 604/295–302, 294; 4/620; 215/343
See application file for complete search history.

(56) References Cited

U.S. PATENT DOCUMENTS

| | | | | | |
|---|---|---|---|---|---|
| 633,297 | A | * | 9/1899 | Wanner | 215/329 |
| 1,654,888 | A | * | 1/1928 | King | 601/13 |
| 1,692,143 | A | * | 11/1928 | Strunz | 604/301 |
| 2,080,268 | A | * | 5/1937 | Harris | 604/298 |
| 2,231,112 | A | * | 2/1941 | Conner | 604/295 |
| 2,283,668 | A | * | 5/1942 | Demsey | 604/301 |
| 2,498,930 | A | * | 2/1950 | Wadsworth | 215/276 |
| 2,585,264 | A | | 2/1952 | Mock | |
| 2,626,606 | A | * | 1/1953 | Campbell | 604/301 |
| 2,705,088 | A | * | 3/1955 | Van Blarcom | 220/259.3 |
| 2,723,040 | A | * | 11/1955 | Merolle | 215/334 |
| 3,064,844 | A | * | 11/1962 | Hoffmann | 215/45 |
| 3,099,361 | A | * | 7/1963 | Ruetz | 215/345 |
| 3,216,632 | A | * | 11/1965 | Dearing | 222/153.07 |
| 3,344,942 | A | * | 10/1967 | Hedgewick | 215/222 |

(Continued)

FOREIGN PATENT DOCUMENTS

| | | |
|---|---|---|
| AU | 437491 | 7/1969 |
| DE | 2540914 | 3/1977 |

(Continued)

*Primary Examiner* — Melanie Hand
*Assistant Examiner* — Paula L Craig
(74) *Attorney, Agent, or Firm* — Douglas E. Jackson; Stites & Harbison PLLC

(57) ABSTRACT

Individual portable device (1) for eye bath, comprising a receptacle (5) with narrow neck (4) enclosing a sterile liquid for eye bath and an eye cup (2) provided with a sleeve interlocked on the neck; an elastically deformable and heat-stable seal (6) has an at least L-shaped section and rests on the rim (7) of the neck of the receptacle; the skirt (6*a*) defining the large leg of the L is clamped between the sleeve of the eye cup and the neck of the receptacle; thus the eye cup (2) is secured to the receptacle (5) in a leaktight manner regardless of the deformations undergone by the neck of the receptacle and the sleeve of the eye cup during heat sterilization treatments.

14 Claims, 2 Drawing Sheets

(56) References Cited

U.S. PATENT DOCUMENTS

| | | | | | |
|---|---|---|---|---|---|
| 3,411,650 | A * | 11/1968 | Mumford | 215/347 |
| 3,480,169 | A * | 11/1969 | Hammes | 215/352 |
| 3,684,125 | A * | 8/1972 | Laurizio | 220/276 |
| 3,788,510 | A * | 1/1974 | Collins | 215/341 |
| 3,812,992 | A * | 5/1974 | Wolf et al. | 215/253 |
| 3,860,152 | A * | 1/1975 | Marti | 222/545 |
| 3,923,183 | A * | 12/1975 | Choksi et al. | 215/251 |
| 3,945,381 | A * | 3/1976 | Silver | 604/301 |
| 4,106,654 | A * | 8/1978 | Jones | 215/329 |
| 4,111,200 | A * | 9/1978 | Sbarra et al. | 604/298 |
| 4,177,905 | A * | 12/1979 | Winchell et al. | 215/246 |
| 4,308,965 | A * | 1/1982 | Dutt | 215/345 |
| 4,366,913 | A * | 1/1983 | Winchell et al. | 215/329 |
| 4,387,819 | A * | 6/1983 | Corsette | 215/273 |
| 4,583,665 | A * | 4/1986 | Barriac | 222/83 |
| 5,007,905 | A * | 4/1991 | Bauer | 604/295 |
| 5,174,460 | A * | 12/1992 | Minnette | 215/335 |
| 5,178,613 | A * | 1/1993 | Gibilisco | 604/294 |
| 5,181,626 | A * | 1/1993 | Daenen et al. | 220/282 |
| 5,188,249 | A * | 2/1993 | Cargile | 215/390 |
| 5,416,973 | A * | 5/1995 | Brown et al. | 30/34.2 |
| 5,454,489 | A * | 10/1995 | Vesborg | 222/109 |
| 5,499,751 | A * | 3/1996 | Meyer | 222/386 |
| 5,588,559 | A * | 12/1996 | Vallet Mas et al. | 222/92 |
| 5,588,564 | A * | 12/1996 | Hutson et al. | 222/383.1 |
| 5,603,436 | A * | 2/1997 | Leoncavallo et al. | 222/525 |
| 5,743,420 | A * | 4/1998 | Loffler et al. | 215/270 |
| 6,540,726 | B1 * | 4/2003 | Follman et al. | 604/294 |
| 6,843,389 | B2 * | 1/2005 | Kasting et al. | 222/111 |
| 7,134,565 | B1 * | 11/2006 | Wan et al. | 215/276 |
| 2002/0153386 | A1 * | 10/2002 | Uetake et al. | 222/1 |
| 2002/0190079 | A1 * | 12/2002 | Hamamoto | 222/105 |
| 2004/0217083 | A1 * | 11/2004 | Mavin et al. | 215/253 |
| 2005/0023293 | A1 * | 2/2005 | Kasting et al. | 222/111 |
| 2005/0139611 | A1 * | 6/2005 | Kubo et al. | 222/189.06 |
| 2005/0165368 | A1 * | 7/2005 | Py et al. | 604/289 |
| 2006/0102583 | A1 * | 5/2006 | Baughman et al. | 215/216 |
| 2008/0067194 | A1 * | 3/2008 | Faurie | 222/189.07 |

FOREIGN PATENT DOCUMENTS

| | | | |
|---|---|---|---|
| DE | 3035211 | | 4/1982 |
| FR | 1448427 | | 9/1965 |
| FR | 2682036 | | 4/1993 |
| FR | 2682873 | | 4/1993 |
| WO | WO 8702237 | * | 4/1987 |
| WO | WO 03/065967 | | 8/2003 |

* cited by examiner

INDIVIDUAL PORTABLE DEVICE FOR EYE BATH

The present application claims priority to French Patent Application No. 06 09629 filed Nov. 3, 2006.

FIELD OF THE INVENTION

The present invention relates to an individual portable device for eye bath, in particular for an eye injured for example on account of having been splashed by a chemical or similar product.

BACKGROUND OF THE INVENTION

The washing of splashes of a chemical product in an eye is a problem which arises continually in laboratories and factories. This problem is still poorly resolved. Specifically, the quality and effectiveness of the washing depend much on the swiftness of intervention after the injury is sustained and the effectiveness of the washing solution employed. Though great progress has been made in the quality of washing solutions, the hardware which enables them to be implemented still remains a brake on obtaining an effective result.

Furthermore, it is necessary, precisely in the context of swift intervention, typically within a timescale of less than one minute, that the injured person himself be able, alone, to wash his affected eye with the appropriate product.

Several devices usable for washing an eye that has been splashed by chemical products are known today. These devices can take the form of a (sterilized) glass flask connected up to tubing terminating in an eye cup. Plastic pouches to which is connected tubing terminating in an eye cup also exist. There also exist plastic bottles filled and closed on line; sterilization is carried out in an aseptic manner and the opening system is obtained by rotation.

These systems exhibit numerous drawbacks or inadequacies as regards their use. For the glass flask, the risk of breakage renders the use thereof problematic; furthermore, they are only usable in a wall mount, and the problem then arises of their going out of date after a duration of six months starting from their installation in a wall mount, as well as the problem of the cleanliness of the eye cup which remains in the open air. The problems posed by plastic pouches are similar. As far as plastic bottles filled and closed on line are concerned, they are not sterilizable in an air/steam autoclave; moreover, the opening process is too lengthy.

Document FR 2 682 036 in the name of the Applicant describes an individual portable device for eye bath, in which the edge of an opening of a reservoir is shaped in a non-planar curvilinear manner, approximating a saddle, to form an eye cup. This device has been designed in view of the constraints set out above and, from this point of view, is entirely satisfactory in use.

However, this known device has been made with a reservoir of small capacity (typically around 50 ml): the small volume of liquid available requires that the eye be washed very swiftly (a few seconds) after the injury is sustained. If one wishes to lengthen the intervention timescale (for example of the order of a minute), it is necessary to employ a much bigger volume of liquid (for example of the order of 500 ml), this involving a much larger reservoir although its opening forming the eye cup should retain the same dimensions. Such a device cannot be manufactured under economic conditions in very large batches from a material suitable for withstanding an air/steam autoclave sterilization process and this device must be manufactured by moulding, implementing particular moulding techniques, which are slow and expensive. The manufacture of these devices cannot therefore be undertaken with all the desirable flexibility in terms of diversification of models of various capacities, nor above all under desirable economic conditions for production in very large batches.

According in particular to documents FR 2 682 873, FR 1 448 427, DE 30 35 211, DE 25 40 914, eye bath devices are known which consist of several elements with in particular a receptacle with narrow neck forming a reservoir for a sterile eye bath liquid and a fitted eye cup furnished with interlocking means comprising a double-walled sleeve with U-shape section suitable for overlapping the rim of the neck while tightly clamping the latter; the neck and at least one wall of the sleeve are equipped with complementary reliefs which ensure axial retention of the eye cup on the neck and leaktightness of the assembly.

However, these known devices are intended to undergo chemical sterilization processes (for example by means of ethylene oxide) or sterilization with gamma rays at ambient temperature. On the other hand, they are not appropriate for withstanding a heat sterilization process (at temperatures of the order of 110 to more than 120° C.) with the assurance of preserving the leaktightness of the assembly of the eye cup to the neck of the receptacle if said receptacle and said eye cup are made of synthetic materials having different thermal behaviours.

Now, the search for manufacturing conditions that are ever more favourable both as regards costs and as regards the products available on the market are today leading precisely to envisaging the production of eye bath devices of said type in which the receptacle and the eye cup are made of thermally incompatible synthetics, but which must be suitable for withstanding a sterilization process carried out thermally, by autoclaving of the air/steam type, while preserving the leaktightness of the assembly of the eye cup to the neck of the receptacle.

SUMMARY OF THE INVENTION

The present invention intends to propose an improved technical solution suitable for solving the problems set forth above that are encountered with the prior art devices, with the aid of an eye cup that is easily adaptable in a leaktight manner to any type of narrow-necked receptacle, and that allows the formation of an individual portable device for eye bath that is easily sterilizable by a thermal process while subsequently preserving the liquid contained in the receptacle under perfectly sterile conditions.

To these ends, the present invention proposes an individual portable device for eye bath, comprising a receptacle provided with a narrow neck enclosing a sterile liquid for eye bath and an eye cup provided with a sleeve suitable for cooperating by interlocking with the neck, which device, being arranged in accordance with the invention, is characterized in that it furthermore comprises a seal made of an elastically deformable material, able to withstand a heat sterilization treatment and that is chemically compatible with the liquid, and in that the seal has an at least L-shaped section resting on the rim of the neck of the receptacle, the skirt defining the large leg of the L being clamped between the sleeve and the neck of the receptacle.

By virtue of this arrangement, the eye cup is secured to the receptacle in a leaktight manner regardless of the deformations undergone by the neck of the receptacle and the sleeve of the eye cup during heat sterilization treatments. The individual portable device is easily adaptable to any type of receptacle furnished with a neck and having any desirable capacity.

The expression narrow-necked receptacle is understood to mean any receptacle, in particular of the bottle or flask type, whose neck exhibits a substantially lesser transverse dimension than that of the body of the receptacle, so that this receptacle can, being made of an appropriate material, be manufactured economically and in very large batches by blowing a preform.

According to a possible embodiment, the seal possesses an L-shaped section resting, via a skirt defining the small leg of the L, on the rim of the neck of the receptacle, the skirt defining the large leg of the L being clamped between the sleeve of the eye cup and the neck of the receptacle.

Although a seal with L-shaped section is technically appropriate to the sought-after aim, in a preferred embodiment provision is made for the seal to possess a U-shaped section overlapping the rim of the neck of the receptacle, one of the skirts defining the U being clamped between the sleeve and the neck of the receptacle. In this case, the seal cooperates in a more stable manner with the neck.

In a concrete exemplary embodiment, it is advantageous for the sleeve of the eye cup to overlap the neck of the receptacle and for it to be the skirt forming the large leg of the L and situated externally to the neck or respectively the external skirt defining the U of the seal which is clamped between the inner face of the sleeve of the eye cup and the outer face of the neck of the receptacle.

Still with the aim of ensuring stable positioning of the seal on the neck of the receptacle in such a way as to maintain optimal leaktightness, it is desirable for the other skirt defining the U to be kept applied tightly against the neck of the receptacle. To do this, it is possible to envisage that the other skirt is pressed elastically against the neck of the receptacle or else, by way of variant, that a ring forming a counter-seal holds the other skirt of the seal; accordingly, provision may be made for the counter-seal to be an annular web which is secured to the sleeve and which is offset radially with respect to the latter, or for the counter-seal to be a cylindrical tubular piece able to be introduced into the internal space of the seal.

In a practical exemplary embodiment, the sleeve of the eye cup comprises at least one relief able to cooperate with a relief of complementary shape provided on the neck of the receptacle, the eye cup being secured by snap-fitting to the neck of the receptacle, thereby simplifying and accelerating the process of mounting the device.

In order to allow the sterilization of the portable device according to the invention, the seal is made of a material able to resist a temperature of between 100 and 130° C. Various materials can meet the stated requirements, in particular EVOPRENE which is a thermoplastic elastomer compound, butyl or silicone.

The provisions in accordance with the invention which have just been set out afford great freedom in choosing the constituent materials of the receptacle and of the eye cup, respectively. In particular, it may be envisaged that the receptacle be made of polypropylene, a material which is currently commonly employed for manufacturing receptacles with a pharmaceutical use and which offers the considerable advantage of allowing narrow-necked receptacles to be manufactured by a blowing process which is more economical than the moulding process. An additional advantage, far from being negligible, resides in the fact that such polypropylene receptacles of various capacities are commonly available on the market and that there is no need, at least for most applications, to call upon specifically manufactured receptacles: the cost of the device is therefore considerably reduced.

In parallel, it is possible to implement an eye cup made of a different material, and in particular preferably that the eye cup be made of polycarbonate, a material which possesses a different coefficient of thermal expansion from that of polypropylene.

BRIEF DESCRIPTION OF THE DRAWINGS

The present invention will now be described with the aid of examples that are solely illustrative and in no way limit the scope of the invention, with reference to the appended drawings in which.

DETAILED DESCRIPTION OF THE INVENTION

Figure 1A:
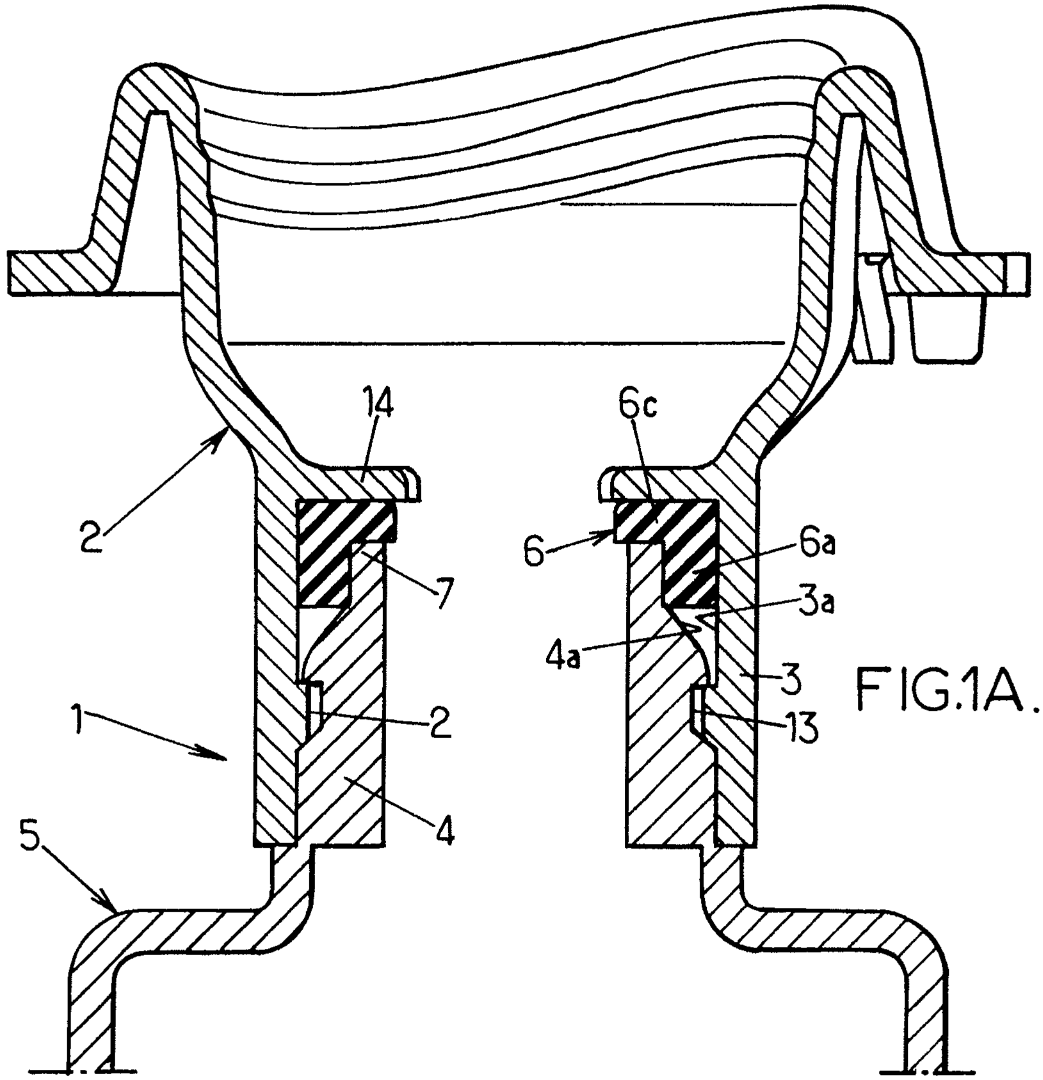
FIG. 1A represents a longitudinal cross-sectional view of a part of an eye bath device arranged according to an embodiment in accordance with the invention.

Represented in FIG. 1 is a cross-sectional view of a part of an individual portable device for eye bath, denoted overall by the reference 1, which comprises an eye cup 2, typically and preferably made of polycarbonate, possessing a sleeve-shaped part 3 for mounting thereof on the neck 4 of a receptacle 5, typically and preferably made of polypropylene, suitable for containing a sterile eye bath liquid.

The receptacle 5 is of any desired capacity enabling it to be easily transported daily by a possible user, for example in a pocket of overalls, a tool bag, a wall mount or a laboratory bench.

Narrow-necked receptacles, made of polypropylene, that can be manufactured by blowing are currently available on the market in various capacities and at very low cost.

The portable device 1 comprises a seal 6 whose section has an at least L-shaped general form, which rests on the rim 7 of the neck 4 of the receptacle 5. The expression at least L-shaped general form is understood to mean a shape exhibiting at least one large leg associated with a transverse return, namely a leg associated with a return according to an L configuration or else two legs flanking a return according to a U configuration.

The seal is made of an elastically deformable material, able to resist sterilization by autoclaving of the air/steam type, namely at a temperature of between 100 and 130° C., and chemically compatible with the liquid contained in the receptacle 5. Numerous materials may meet these requirements, in particular: natural rubber, EPDM (ethylene-propylene-diene monomer terpolymer), butadiene-styrene, neoprene, EVOPRENE which is a thermoplastic elastomer compound, nitrile, urethane, silicone, fluoroelastomer, latex, vulcanized thermoplastics (VTP), elastomer thermoplastics (ETP), polyacrylate, epichlorohydrine polymer, butyl, NBR (acrylonitrile-butadiene rubber)-nitrile VTP copolyester, VTP-EPDM.

Practically, the seal is preferably made of a material that is commercially available under the name EVOPRENE which is a thermoplastic elastomer compound) or of butyl or of silicone.

In the embodiment illustrated in FIG. 1, the seal 6 possesses a general L-shaped section. The skirt 6*a* is clamped between the sleeve 3 of the eye cup 2 and the neck 4 of the receptacle 5, whereby the eye cup 2 is secured to the receptacle 5 in a leaktight manner despite the sterilization heat treatment (typically at a temperature of between 100 and 130° C.). The skirt 6*c* forming said return rests on the rim 7 of the neck.

In the specific exemplary embodiment illustrated in FIG. 1A, the sleeve 3 overlaps the neck 4 of the receptacle 5 and the skirt 6*a* of the seal 6 is clamped between the inner face 3*a* of the sleeve 3 of the eye cup 2 and the outer face 4*a* of the neck 4 of the receptacle 5. The seal 6 is here shaped with the skirt 6*c* extending radially inwards.

Figure 1B:
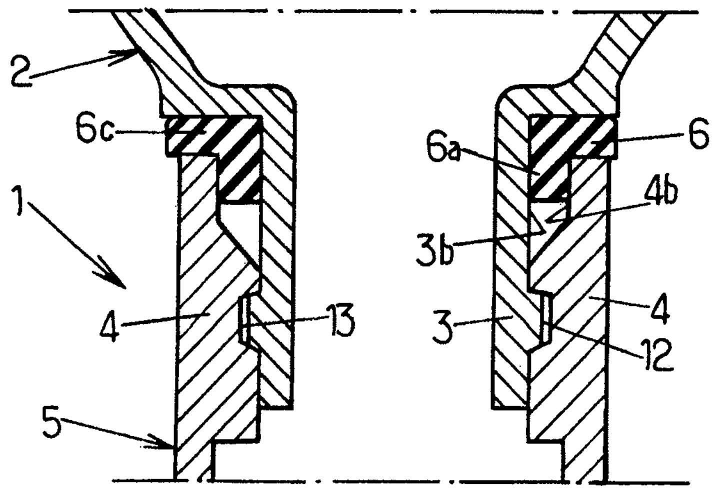
FIG. 1B is a partial cross-sectional view showing a variant of the arrangement of FIG. 1A.

A variant embodiment of the above provisions is shown in FIG. 1B. This variant consists in the sleeve 3 of the eye cup 2 having a smaller diameter than that of the neck 4 of the receptacle 5 and being sunk into the latter; in this case, the skirt 6*a* of the seal 6 is clamped between the outer face 3*b* of the sleeve 3 of the eye cup 2 and the inner face 4*b* of the neck 4 of the receptacle 5. The seal 6 is here shaped with the skirt 6*c* extending radially outwards.

Figure 2A:
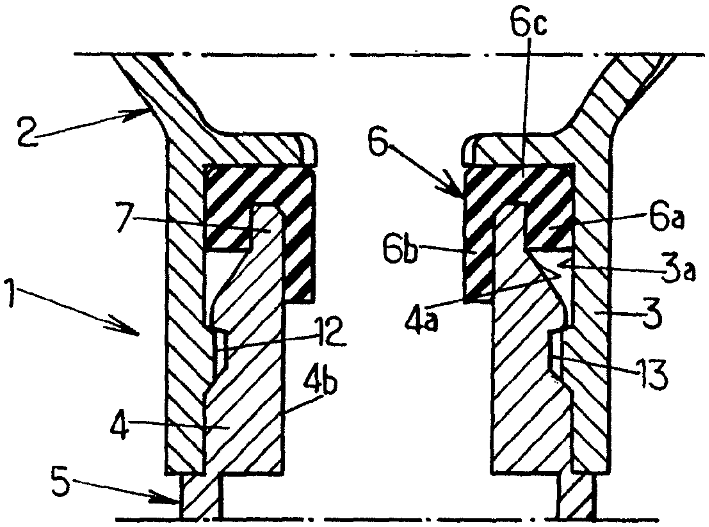
FIGS. 2A to 2C are partial views of various alternative embodiments of an eye bath device arranged according to another, currently preferred, embodiment in accordance with the invention.
Figure 2B:
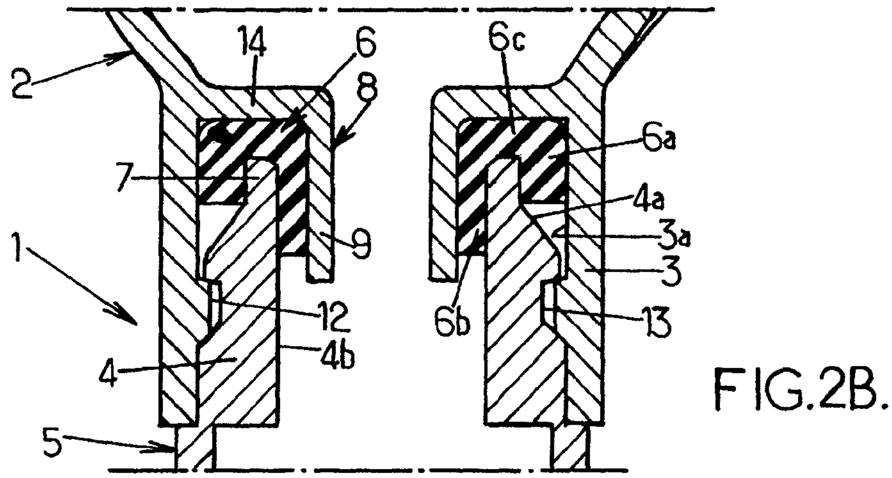
Figure 2C:
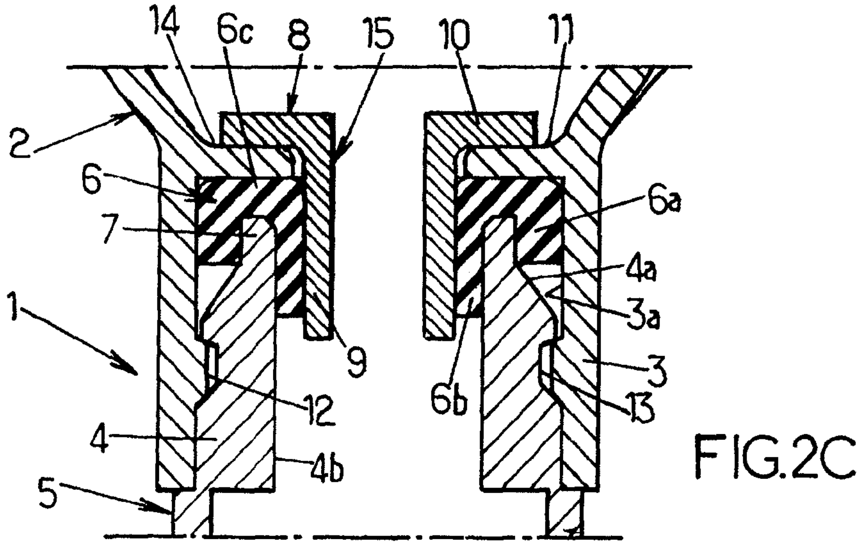

In FIGS. 2A to 2C are shown several variant embodiments of another embodiment, which is currently preferred in practice, consisting of the seal 6 having a general U-shaped section and being defined by two skirts 6*a* and 6*b*, the seal 6 overlapping the rim 7 of the neck 4 of the receptacle 5; the reference 6*c* denoting said return skirt is then applied to the bottom of the U.

In the variant embodiment shown in FIG. 2A (the sleeve 3 of the eye cup 2 being assumed to cover over the neck 4 of the receptacle 5), the external skirt 6*a* of the seal 6 is clamped between the outer face 4*a* of the neck 4 of the receptacle 5 and the inner face 3*a* of the sleeve 3 of the eye cup 2. The other skirt 6*b* remains applied elastically against the inner face 4*b* of the neck 4 of the receptacle 5. To ensure correct holding and correct compression of the seal, the sleeve 3 is provided internally with a web 14 of radial extent, which extends preferably annularly in a continuous manner; this web 14 is situated opposite the rim 7 of the neck 4 of the receptacle 5 and compresses the small return leg 6*b* of the seal 6 in the axial direction.

If one wishes to make certain that the other skirt 6*b* of the seal 6 bears against the inner face 4*b* of the neck 4 and to strengthen the locking of the seal 6 onto the rim 7 of the neck 4, it is possible to provide for this purpose the implementation of a mechanical means in the form of a counter-seal 8 which is able to compress the seal 6. Such a counter-seal may in a simple manner take the form of an axisymmetric cylindrical ring 9 introduced into the central free space of the seal 6 and able to clamp the inner skirt 6*b* against the inner face 4*b* of the neck 4 of the receptacle 5.

In the variant embodiment shown in FIG. 2B, the ring 9 is an annular web secured to the sleeve 4 and offset radially inwards with respect to the latter in such a way as to define a trough in which the other skirt 6*b* is imprisoned and clamped.

In the variant embodiment shown in FIG. 2C, the ring 9 is an independent piece added into the internal space of the seal. As illustrated, it may be a piece 15 having an axisymmetric cylindrical annular body which constitutes said ring 9 and which is surmounted by a widened head 10, in particular circular, able to be pressed against the bottom 11 of the eye cup 2 (which bottom 11 may be the upper face of said web 14).

For mechanically securing the eye cup to the neck 4 of the receptacle 5, the sleeve 3 of the eye cup 2 comprises an internal annular rib 12 able to cooperate with an annular groove 13 provided on the outer face 4*a* of the neck 4 of the receptacle 5 (it being possible for the rib and groove to be positioned in reverse fashion).

Additionally, a stopper (not represented in the figure but of a type known per se) is fixed in a leaktight manner to the eye cup 2.

It is understood that, alternatively, it is possible to envisage a reverse arrangement relative to that just described with reference to FIGS. 2A to 2C, with the sleeve 3 of the eye cup 2 being inserted into the neck 4 of the receptacle 5 with the internal skirt 6*b* of the U-shaped seal 6 being clamped between the neck 4 and the sleeve 3 and pressed against the inner face 4*a* of the neck 4; the counter-seal 8, if it is implemented, then takes the form of a ring external to the neck 4.

What is claimed is:

1. An individual portable device for eye bath, comprising:

a receptacle provided with a narrow neck including a vertical neck portion terminating at an upper rim, the receptacle enclosing a sterile liquid for eye bath, and an eye cup provided with an axial sleeve suitable for cooperating by interlocking with the neck, the eye cup furthermore comprising a discrete seal a) made of an elastically deformable material, b) able to withstand a heat sterilization treatment, and c) chemically compatible with the liquid, and wherein the seal possesses an at least L-shaped section resting on the upper rim of the neck of the receptacle, the L-shaped section including a vertical skirt defining the large leg of the L-shaped section which vertical skirt is radially clamped between the axial sleeve of the eye cup and the vertical neck portion of the receptacle, whereby the eye cup is secured to the receptacle in a leaktight manner by the radial clamping of the vertical skirt regardless of the deformations presented by the neck of the receptacle and the sleeve of the eye cup after heat sterilization treatments.

2. The device according to claim 1, wherein said sleeve of the eye cup comprises at least one relief able to cooperate with a relief of complementary shape provided on the vertical neck portion of the receptacle, the eye cup being secured by snap-fitting of the sleeve to the neck of the receptacle.

3. The device according to claim 1, wherein said seal is made of a material able to resist a temperature of between 100 and 130° C.

4. The device according to claim 1, wherein said seal is made of a material chosen from among a thermoplastic elastomer, butyl or silicone.

5. The device according to claim 1, wherein said receptacle is made of polypropylene.

6. The device according to claim 5, wherein said eye cup is made of polycarbonate.

7. The device according to claim 1, wherein said seal has an L-shaped section resting, via a horizontal skirt defining the small leg of the L, on the rim of the neck of the receptacle, the horizontal skirt being clamped vertically between the sleeve of the eye cup and the rim of the neck of the receptacle.

8. The device according to claim 7, wherein said seal has a second vertical skirt so that the seal has an overall U-shaped section with the horizontal skirt overlapping the rim of the neck of the receptacle.

9. The device according to claim 7, wherein said sleeve of the eye cup overlaps the neck of the receptacle, and wherein the vertical skirt of the L-shaped section is situated externally to the vertical neck portion, whereby the vertical skirt is radially clamped between an inner face of the sleeve of the eye cup and an outer face of the vertical neck portion of the receptacle.

10. The device according to claim 8, wherein said U-shaped sleeve of the eye cup overlaps the neck of the receptacle, and wherein an external one of the first-mentioned vertical skirt and second vertical skirt is radially clamped between an inner face of the sleeve of the eye cup and an outer face vertical neck portion of the receptacle.

11. The device according to claim 8, wherein an internal one of the first-mentioned vertical skirt and the second vertical skirt of the U-shaped seal is radially pressed elastically against the vertical neck portion of the receptacle.

12. The device according to claim 8, wherein the eye cup further comprises a ring forming a counter-seal which radially presses the second skirt of the U-shaped seal against the vertical neck portion of the receptacle.

13. The device according to claim 12, wherein the ring is an annular web secured to the sleeve and offset radially with respect to the sleeve.

14. The device according to claim 8, wherein the eye cup further comprises a ring forming a counter-seal which presses the second skirt of the U-shaped seal radially against the vertical neck portion of the receptacle, and wherein the ring is an independent piece added on in an internal space of the seal.

* * * * *